(12) United States Patent
Huntsman et al.

(10) Patent No.: US 8,979,927 B2
(45) Date of Patent: Mar. 17, 2015

(54) SPINAL IMPLANT WITH STAPLES

(75) Inventors: Kade T. Huntsman, Holladay, UT (US); Brent A. Felix, Sandy, UT (US); Ronald K. Groberg, Clearfield, UT (US)

(73) Assignee: Innovasis, Inc., Salt Lake City, UT (US)

( * ) Notice: Subject to any disclaimer, the term of this patent is extended or adjusted under 35 U.S.C. 154(b) by 399 days.

(21) Appl. No.: 12/621,217

(22) Filed: Nov. 18, 2009

(65) Prior Publication Data

US 2011/0118840 A1 May 19, 2011

(51) Int. Cl.
  *A61F 2/44* (2006.01)
  *A61F 2/30* (2006.01)
  *A61F 2/46* (2006.01)

(52) U.S. Cl.
  CPC ......... *A61F 2/4455* (2013.01); *A61F 2002/448* (2013.01); *A61F 2/30749* (2013.01); *A61F 2/30965* (2013.01); *A61F 2002/30062* (2013.01); *A61F 2002/30131* (2013.01); *A61F 2002/30364* (2013.01); *A61F 2002/30372* (2013.01); *A61F 2002/30459* (2013.01); *A61F 2002/305* (2013.01); *A61F 2002/30576* (2013.01); *A61F 2002/30604* (2013.01); *A61F 2002/30904* (2013.01); *A61F 2002/4475* (2013.01); *A61F 2002/4629* (2013.01); *A61F 2210/0004* (2013.01); *A61F 2220/0008* (2013.01); *A61F 2220/0025* (2013.01); *A61F 2220/0033* (2013.01); *A61F 2220/0066* (2013.01); *A61F 2230/0013* (2013.01); *A61F 2310/00017* (2013.01); *A61F 2310/00023* (2013.01)
  USPC ........................................... 623/17.11

(58) Field of Classification Search
  CPC .................................................. A61F 2002/448
  USPC ............................................ 623/17.11–17.16
  See application file for complete search history.

(56) References Cited

U.S. PATENT DOCUMENTS

| | | | | |
|---|---|---|---|---|
| 4,570,623 | A * | 2/1986 | Ellison et al. | 606/75 |
| 5,108,422 | A * | 4/1992 | Green et al. | 606/219 |
| 5,395,372 | A * | 3/1995 | Holt et al. | 606/86 B |
| 5,522,899 | A * | 6/1996 | Michelson | 606/279 |
| 5,562,736 | A * | 10/1996 | Ray et al. | 606/86 A |
| 5,702,455 | A * | 12/1997 | Saggar | 623/17.15 |
| 5,776,199 | A * | 7/1998 | Michelson | 623/17.16 |
| 6,120,503 | A * | 9/2000 | Michelson | 606/86 A |
| 6,136,001 | A * | 10/2000 | Michelson | 606/247 |
| 6,149,650 | A * | 11/2000 | Michelson | 623/17.16 |
| 6,287,308 | B1 * | 9/2001 | Betz et al. | 606/263 |
| 6,325,805 | B1 * | 12/2001 | Ogilvie et al. | 606/75 |
| 6,364,880 | B1 * | 4/2002 | Michelson | 606/247 |
| 6,447,547 | B1 * | 9/2002 | Michelson | 623/17.16 |
| 6,478,823 | B1 * | 11/2002 | Michelson | 623/17.16 |
| 6,485,517 | B1 * | 11/2002 | Michelson | 623/17.11 |
| 6,558,423 | B1 * | 5/2003 | Michelson | 623/17.11 |
| 6,576,017 | B2 * | 6/2003 | Foley et al. | 623/17.16 |
| 6,773,437 | B2 * | 8/2004 | Ogilvie et al. | 606/75 |
| 7,033,394 | B2 * | 4/2006 | Michelson | 623/17.11 |

(Continued)

*Primary Examiner* — Thomas J Sweet
*Assistant Examiner* — Stuart S Bray
(74) *Attorney, Agent, or Firm* — Workman Nydegger (57) ABSTRACT

A spinal implant having a spinal cage and a plurality of staples. The spinal cage is configured to be positioned in an intervertebral space between adjacent vertebrae. The plurality of staples are moveably disposed on the spinal cage and configured to be inserted into the adjacent vertebrae so as to secure the spinal cage in the intervertebral space when the spinal cage is positioned therein. A method of securing the spinal implant within the intervertebral space.

17 Claims, 12 Drawing Sheets

(56) References Cited

U.S. PATENT DOCUMENTS

| | | | |
|---|---|---|---|
| 7,041,135 B2* | 5/2006 | Michelson | 623/17.11 |
| 7,255,698 B2* | 8/2007 | Michelson | 606/247 |
| 7,344,539 B2* | 3/2008 | Serhan et al. | 623/13.11 |
| 7,534,265 B1* | 5/2009 | Boyd et al. | 623/17.11 |
| 7,621,938 B2* | 11/2009 | Molz, IV | 606/246 |
| 7,637,951 B2* | 12/2009 | Michelson | 623/17.11 |
| 7,637,954 B2* | 12/2009 | Michelson | 623/17.11 |
| 7,887,595 B1* | 2/2011 | Pimenta | 623/17.16 |
| 7,910,690 B2* | 3/2011 | Ringeisen et al. | 528/502 D |
| 7,914,530 B2* | 3/2011 | Michelson | 606/52 |
| 8,343,220 B2* | 1/2013 | Michelson | 623/17.11 |
| 8,353,913 B2* | 1/2013 | Moskowitz et al. | 606/86 A |
| 8,353,959 B2* | 1/2013 | Michelson | 623/17.11 |
| 8,403,986 B2* | 3/2013 | Michelson | 623/17.11 |
| 2002/0007184 A1* | 1/2002 | Ogilvie et al. | 606/61 |
| 2002/0019636 A1* | 2/2002 | Ogilvie et al. | 606/75 |
| 2002/0055781 A1* | 5/2002 | Sazy | 623/17.11 |
| 2002/0095155 A1* | 7/2002 | Michelson | 606/61 |
| 2002/0099378 A1* | 7/2002 | Michelson | 606/61 |
| 2002/0099444 A1* | 7/2002 | Boyd et al. | 623/17.16 |
| 2002/0143329 A1* | 10/2002 | Serhan et al. | 606/61 |
| 2003/0023307 A1* | 1/2003 | Michelson | 623/17.11 |
| 2003/0065396 A1* | 4/2003 | Michelson | 623/17.15 |
| 2003/0074075 A1* | 4/2003 | Thomas et al. | 623/17.16 |
| 2003/0078668 A1* | 4/2003 | Michelson | 623/17.16 |
| 2003/0135279 A1* | 7/2003 | Michelson | 623/17.16 |
| 2003/0149482 A1* | 8/2003 | Michelson | 623/17.11 |
| 2003/0199983 A1* | 10/2003 | Michelson | 623/17.16 |
| 2003/0233147 A1* | 12/2003 | Nicholson et al. | 623/17.16 |
| 2004/0034353 A1* | 2/2004 | Michelson | 606/61 |
| 2004/0210313 A1* | 10/2004 | Michelson | 623/17.11 |
| 2005/0033433 A1* | 2/2005 | Michelson | 623/17.11 |
| 2005/0038513 A1* | 2/2005 | Michelson | 623/17.11 |
| 2005/0246021 A1* | 11/2005 | Ringeisen et al. | 623/17.11 |
| 2006/0052870 A1* | 3/2006 | Ferree | 623/17.11 |
| 2006/0241764 A1* | 10/2006 | Michelson | 623/17.11 |
| 2007/0185580 A1* | 8/2007 | Posel | 623/17.16 |
| 2007/0239278 A1* | 10/2007 | Heinz | 623/17.15 |
| 2007/0250166 A1* | 10/2007 | McKay | 623/17.11 |
| 2008/0033440 A1* | 2/2008 | Moskowitz et al. | 606/72 |
| 2008/0051902 A1* | 2/2008 | Dwyer | 623/17.16 |
| 2008/0058939 A1* | 3/2008 | Hughes et al. | 623/17.15 |
| 2008/0154368 A1* | 6/2008 | Justis et al. | 623/11.11 |
| 2008/0177307 A1* | 7/2008 | Moskowitz et al. | 606/246 |
| 2008/0294261 A1* | 11/2008 | Pauza et al. | 623/17.16 |
| 2008/0300634 A1* | 12/2008 | Gray | 606/280 |
| 2008/0300685 A1* | 12/2008 | Carls et al. | 623/17.11 |
| 2009/0048675 A1* | 2/2009 | Bhatnagar et al. | 623/17.16 |
| 2009/0234455 A1* | 9/2009 | Moskowitz et al. | 623/17.11 |
| 2010/0030334 A1* | 2/2010 | Molz, IV | 623/17.11 |
| 2010/0036496 A1* | 2/2010 | Yu et al. | 623/17.14 |
| 2010/0042218 A1* | 2/2010 | Nebosky et al. | 623/17.12 |
| 2010/0145463 A1* | 6/2010 | Michelson | 623/17.16 |
| 2010/0168798 A1* | 7/2010 | Clineff et al. | 606/279 |
| 2010/0217393 A1* | 8/2010 | Theofilos | 623/17.11 |
| 2011/0118842 A1* | 5/2011 | Bernard et al. | 623/17.11 |
| 2011/0125267 A1* | 5/2011 | Michelson | 623/17.11 |
| 2011/0178599 A1* | 7/2011 | Brett | 623/17.16 |
| 2011/0295327 A1* | 12/2011 | Moskowitz et al. | 606/86 A |
| 2011/0295371 A1* | 12/2011 | Moskowitz et al. | 623/17.16 |
| 2012/0010714 A1* | 1/2012 | Moskowitz et al. | 623/17.16 |
| 2012/0078371 A1* | 3/2012 | Gamache et al. | 623/17.16 |
| 2012/0078373 A1* | 3/2012 | Gamache et al. | 623/17.16 |
| 2012/0203348 A1* | 8/2012 | Michelson | 623/17.16 |
| 2012/0277871 A1* | 11/2012 | Theofilos | 623/17.16 |
| 2013/0018469 A1* | 1/2013 | Moskowitz et al. | 623/17.16 |
| 2013/0023991 A1* | 1/2013 | Moskowitz et al. | 623/17.16 |
| 2013/0053962 A1* | 2/2013 | Moskowitz et al. | 623/17.16 |
| 2013/0218279 A1* | 8/2013 | Michelson | 623/17.16 |
| 2013/0282017 A1* | 10/2013 | Moskowitz et al. | 606/99 |

* cited by examiner

SPINAL IMPLANT WITH STAPLES

BACKGROUND OF THE INVENTION

1. The Field of the Invention

The present invention relates generally to surgical devices and methods for supporting bone or other tissues and, more specifically, to surgical devices and methods for fusing adjacent vertebrae or other bones.

2. The Relevant Technology

The spinal column is made up of thirty-three vertebrae, each separated by an intervertebral disc. Each disc is slightly compressible, thereby allowing the vertebra above a disc to move relative to the vertebra below the disc. This unique design allows the spine to bend in many directions. The intervertebral discs absorb pounding and compressive forces throughout the lifetime of a person. Through disease, trauma, or normal wear, an intervertebral disc can become damaged or ruptured, thereby creating instability that can lead to pain and loss of function. Such persons often turn to surgery to remove the damaged disc and fuse the corresponding adjacent vertebrae together.

During surgery, the damaged disc is removed and a spinal fusion implant is inserted to replace the damaged disc and restore the spacing between the vertebrae. The spinal implant typically has a thickness corresponding to the thickness of the disc being removed and has openings extending therethrough.

Although there are many different implants that have been used to fuse vertebrae together, conventional implants can suffer from a number of shortcomings. For example, many conventional implants are not rigidly attached to the adjacent vertebrae. As such the implant can potentially move after implantation to a less than optimum location. Other conventional implants are rigidly attached to the vertebrae using screws. While this alleviates the problem of the implant moving after implantation, the manipulating the screws during implantation can be difficult and time consuming.

Furthermore, many conventional intervertebral implants are not stand alone devices; that is, the implant requires external components for the implant to work correctly. For example, many implants require a detached screw to attach the implant to the bone; others require a rod or plate to interconnect the implant to other implants. These external components can make the surgery more complex and can lead to lost parts.

Accordingly, it would be an improvement in the art to provide a spinal implant that solves some or all of the above problems and/or other limitations known in the art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

As used in the specification and appended claims, directional terms, such as "up," "down," "left," "right," "upward," and "downward" are used herein solely to indicate relative directions in viewing the drawings and are not intended to limit the scope of the claims in any way.

Figure 1:
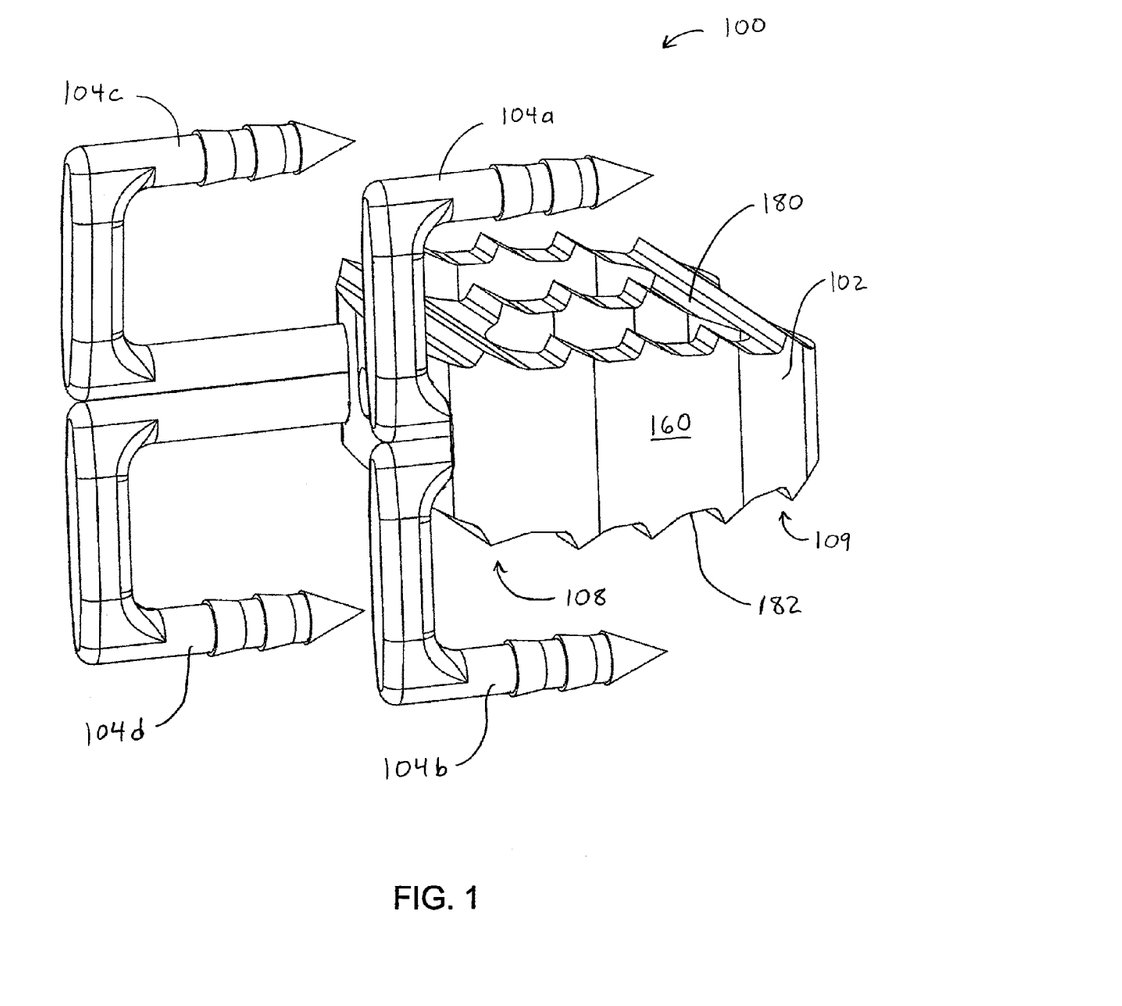
FIG. 1 is a perspective view of one embodiment of a spinal implant according to the present invention having a spinal cage and a plurality of staples.

The present invention relates to stand-alone spinal implants and methods of use that include staples to secure the spinal implant to adjacent vertebrae. Depicted in FIG. 1 is one embodiment of a spinal implant 100 incorporating features of the present invention. Spinal implant 100 comprises a spinal cage 102 and a plurality of staples 104 movably attached thereto.

Spinal cage 102 is designed for placement between bones and/or pieces of bone to facilitate fusing of the bone matter together. For example, spinal cage 102 can be placed between adjacent vertebrae in the spine to facilitate fusing of the vertebrae together.

Spinal cage 102 comprises a top surface 180 and an opposing bottom surface 182, with a perimeter exterior side surface 160 extending therebetween. The top and bottom surfaces 180 and 182 can be substantially parallel with each other or can taper towards one end. For example, in the depicted embodiment, the spinal cage 102 extends between a proximal end 108 and a tapered distal end 109. Other shapes are also possible.

Figure 2:
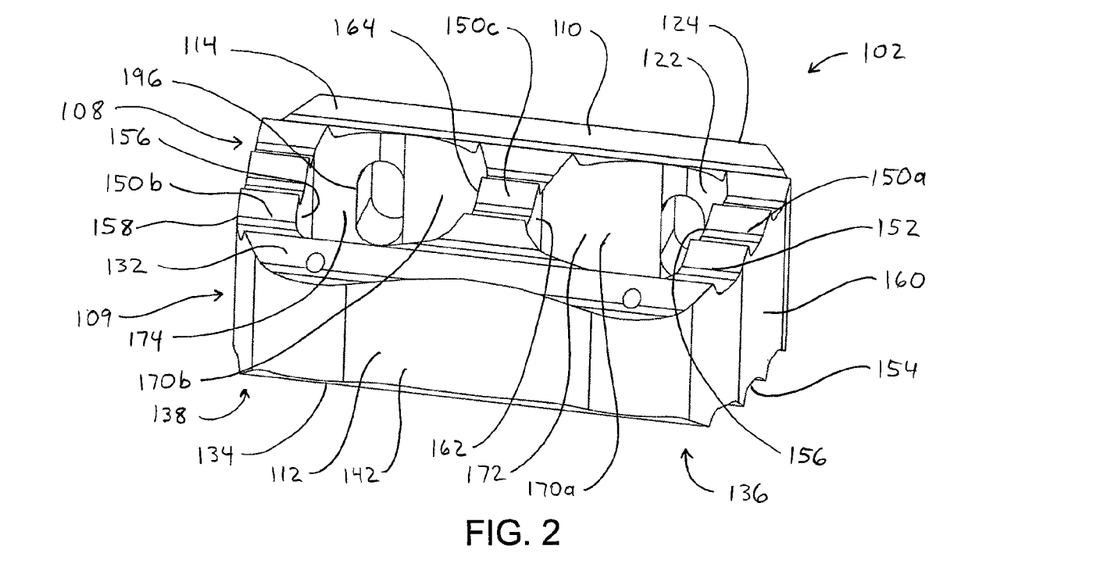
FIGS. 2 and 3 are perspective views of the spinal cage shown in FIG. 1.
Figure 3:
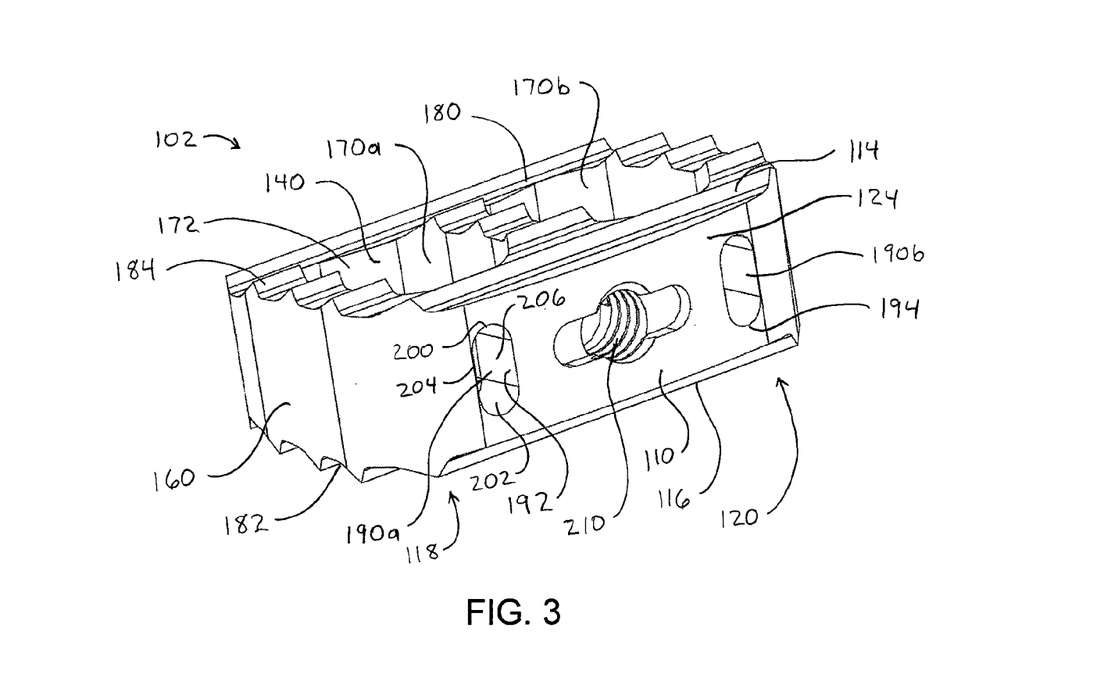

Turning to FIGS. 2 and 3, one or more holes 190 are formed on side surface 160 that extend laterally into spinal cage 102 and are configured to receive portions of one or more staples, as discussed below. One or more openings 170 can also extend completely through spinal cage 102 between top and bottom surfaces 180 and 182. These openings 170 can intersect with the one or more holes 190, causing a lip or edge to be formed at the intersection. For example, in the depicted embodiment a pair of through holes 190a and 190b extend into spinal cage 102 from side surface 160 so as to respectively intersect a pair of openings 170a and 170b, causing edges 196 to be formed therebetween. In the depicted embodiment the holes 190 extend distally into the spinal cage 102 from the proximal end 108 thereof.

Spinal cage 102 can further be defined as comprising a proximal end wall 110 and a spaced apart distal end wall 112 with a plurality of spaced apart beams 150 extending therebetween. Proximal end wall 110 comprises a top surface 114 and an opposing bottom surface 116 that each extend from a first end 118 to a spaced apart second end 120 and from an interior side surface 122 to a spaced apart exterior side surface 124. Similarly, distal end wall 112 also comprises a top surface 132 and an opposing bottom surface 134 that each extend from a first end 136 to a spaced apart second end 138 and from an interior side surface 140 to a spaced apart exterior side surface 142. The proximal and distal end walls 110, 112 are positioned to be generally parallel to each other so that the interior side surfaces 122, 140 of each wall face each other.

In the depicted embodiment, spinal cage 102 has three beams 150a-150c extending between the proximal and distal end walls. Each beam 150 has a top surface 152 and an opposing bottom surface 154 with an interior side surface 156 and an exterior side surface 158 extending therebetween on either side of the beam 150. First beam 150a extends between the interior side surfaces 122 and 140 at the first ends 118, 136 of the proximal and distal end walls 110, 112. Second beam 150b extends between the interior side surfaces 122 and 140 at the second ends 120, 138 of the proximal and distal end walls 110, 112. The proximal end wall 110, distal end wall 112, and first and second beams 150a, 150b are situated such that the exterior surfaces of each collectively form the perimeter exterior side surface 160 of the spinal cage 102.

A third beam 150c extends between the interior side surfaces 122, 140 of the proximal and distal end walls 110, 112. Third beam 150c has two side surfaces 162 and 164 and is disposed between and spaced apart from the first and second beams 150a, 150b. As a result, the two openings 170a and 170b are formed in spinal cage 102 on either side of third beam 150c. The first opening 170a is bounded by a first bounding surface 172, which comprises the interior surface 156 of the first beam 150a, portions of the interior side surfaces 122, 140 of the proximal and distal end walls 110, 112, and one of the side surfaces 162 of third beam 150c. The second opening 170b is bounded by a second bounding surface 174, which comprises the interior surface 156 of the second beam 150b, second portions of the interior side surfaces 122, 140 of the proximal and distal end walls 110, 112, and the other of the side surfaces 164 of third beam 150c.

Figure 4A:
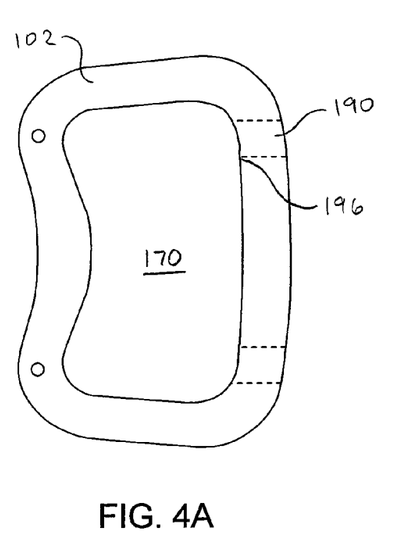
FIGS. 4A and 4B are top views of spinal cages showing alternative arrangements of openings extending therethrough.

In some embodiments third beam 150c is omitted causing only one opening 170 to be formed in spinal cage 102, as shown in FIG. 4A. In still other embodiments the opening or openings 170 do not extend completely through the top surface 180 and/or the bottom surface 182 but instead form an enclosed chamber or cavity. In these alternative embodiments, an edge 196 can still be formed between the opening, cavity, or chamber and the holes 190. In other embodiments, opening 170 is much smaller so as to not intersect holes 190, or is omitted altogether, as respectively shown in FIGS. 4B and 4C.

The proximal end wall 110, the distal end wall 112, and the beams 150 are integrally formed as a single unitary member so that the top surfaces 114, 132, 152 of those components collectively form the top surface 180 of the spinal cage 102 while the bottom surfaces 116, 134, 154 of those components collectively form the bottom surface 182 of the spinal cage 102. If desired, the top surface 180 and/or bottom surface 182 of the spinal cage 102 can have formed thereon or attached thereto surface features that will help the spinal cage 102 remain within the human body, once the implant 100 is positioned therein. For example, in the depicted embodiment, a plurality of raised ridges or barbs 184 running in a direction substantially parallel to the proximal and distal end walls 110, 112 are formed on the top and bottom surfaces 180, 182 of the spinal cage 102.

Continuing with FIGS. 2 and 3, as noted above spinal cage 102 includes a pair of through holes 190a and 190b that extend into spinal cage 102 from side surface 160. In the depicted embodiment, the through holes 190a and 190b are formed on proximal end wall 110 and extend generally parallel to each other between exterior side surface 124 and interior side surface 122. Each through hole 190 is bounded by an internal sidewall 192 extending between an edge 194 formed with exterior side surface 124 and the edge 196 formed with interior side surface 122. The through holes 190 are positioned on proximal end wall 110 such that each of the through holes 190 communicates with a different one of the openings 170. That is, through hole 190a extends through proximal end wall 110 between the exterior side surface 124 of proximal end wall 110 and first bounding surface 172 of first opening 170a. Conversely, through hole 190b extends through proximal end wall 110 between the exterior surface 124 of proximal end wall 110 and second bounding surface 174 of second opening 170b. In embodiments where there is only one opening 170, both through holes 190a and 190b can extend into the same opening 170.

Each through hole 190 is shaped so as to be able to receive and retain a pair of staples 104 while allowing some rotational movement of the staples 104, as discussed in more detail below. For example, in the depicted embodiment, each through hole 190 is generally formed on proximal end wall 110 as a circular cylinder that has been laterally stretched. That is, internal sidewall 192 comprises a pair of semicircular portions 200, 202 on either end of through hole 190 that are connected by two generally parallel opposing side portions 204, 206. The width of the through hole 190 (i.e., the distance between the side portions 204 and 206) is generally equal to the diameter of the semicircular portions 200 and 202. The height of the through hole 190 (i.e., the farthest distance between the internal sidewall 192 comprising the semicircular portions 200 and 202) is generally equal to twice the width of the through hole. This is to allow space for two staples 104 to be inserted into the through hole 190, as discussed in more detail below. Other dimensions can also be used.

Figure 5A:
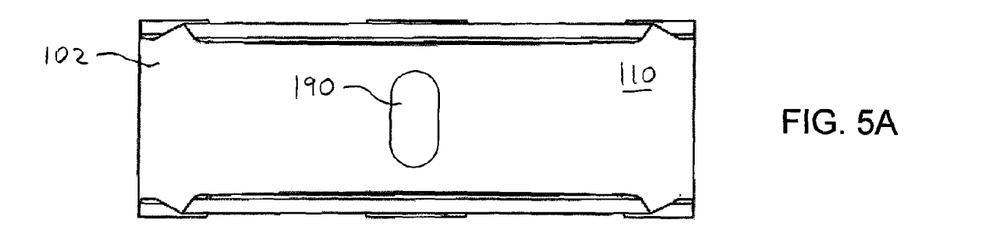
FIGS. 5A-5D are end views of spinal cages showing alternative arrangements of through holes formed thereon.
Figure 5B:
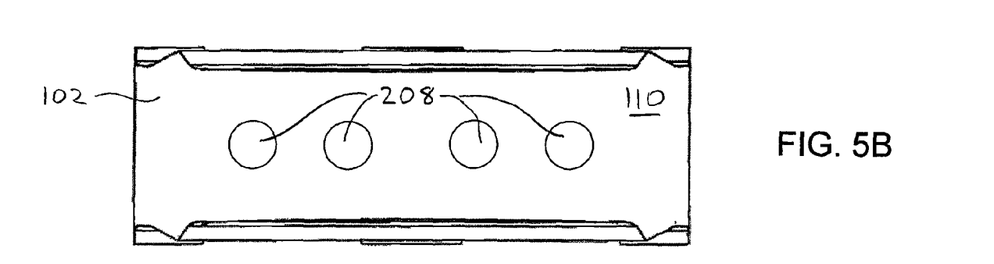
Figure 5C:
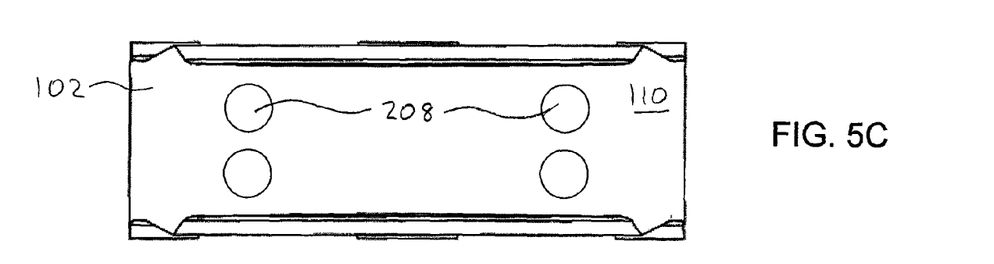
Figure 5D:
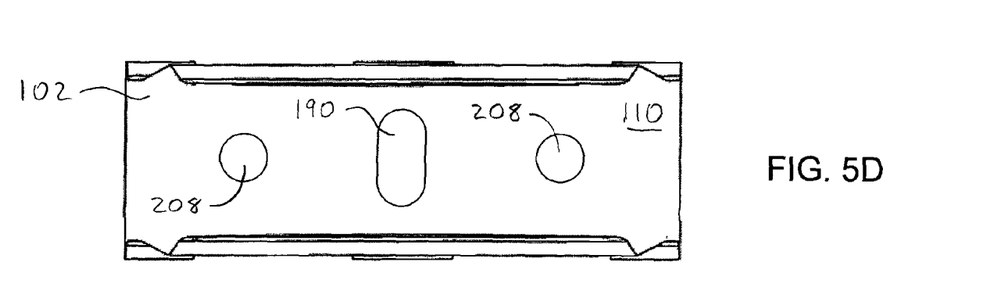

In alternative embodiments, one or more of the through holes can be sized and positioned so that only a single staple 104 can be received therein. FIGS. 5A-5D show examples of different configurations of through holes that can be used in various embodiments of the present invention. For example, in FIG. 5A, only a single through hole 190 capable of receiving two staples is formed on proximal end wall 110. Although shown in the center of proximal end wall 110, it is appreciated that through hole 190 can be positioned anywhere on proximal end wall 110. FIGS. 5B and 5C show embodiments having through holes 208 that are each sized to allow only a single staple 104 to be received therein. Accordingly, each through hole 208 is generally circular in shape. The through holes 208 can be aligned in a single row, as shown in FIG. 5B, or can be positioned in a plurality of rows, as shown in FIG. 5C. Other configurations are also possible. FIG. 5D shows an embodiment in which a combination of through holes 190 and 208 are used. It is appreciated that the embodiments shown in FIGS. 5A-5D are exemplary only; other configurations are also possible.

Figure 4B:
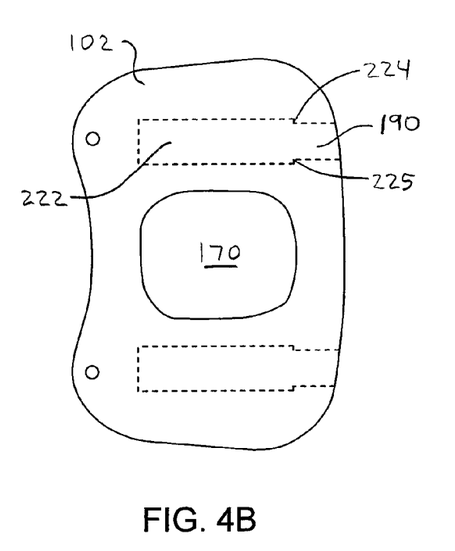
Figure 4C:
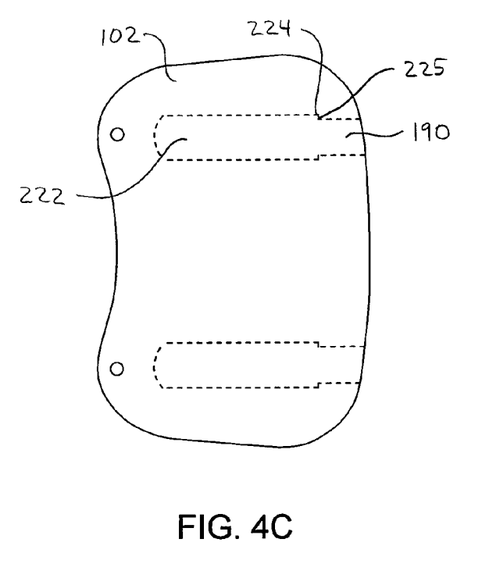
FIG. 4C shows an embodiment of a spinal cage without an opening extending therethrough.

In addition, through holes 190 and/or 208 may not intersect with opening or openings 170, such as in the embodiments shown in FIGS. 4B and 4C. In those cases, a bore 222 is formed at the end of through hole 190 or 208 that extends distally into spinal cage 102. The bore can include a lip 224 containing an edge 225 similar to edge 196 for use in retaining the staples 104.

Spinal cage 102 can also include means for receiving an inserter device. For example, as shown in FIG. 3, the means for receiving an inserter device is a threaded bore 210 formed on the exterior side surface 124 of proximal end wall 110. The bore 210 can be used by an inserter device (not shown) to help insert the spinal cage 102 between vertebrae during installation. The inserter device can be threaded into the bore 210 before installation of the spinal cage 102 and then used to guide the spinal cage 102 into position. Once the spinal cage 102 has been installed, the inserter device can then be removed from the spinal cage 102 by unthreading. It is appreciated that threaded bore 210 is only one example of a means for receiving an inserter device. Other examples of means for receiving an inserter device can include a bayonet mount, a clip mount, a friction fit, or other conventional connections, as is known in the art. Furthermore, although the means for receiving an inserter device is depicted in the center of proximal end wall 110, this is not required.

Spinal cage 102 is typically made from a medical grade biocompatible material. In one embodiment, spinal cage 102 is formed from a polyetheretherketone (PEEK) polymer that can be reinforced with a fiber, such as carbon fiber, and/or other additives. In alternative embodiments, spinal cage 102 can be formed from medical grade biocompatible metals, alloys, polymers, ceramics, or other materials that have adequate strength. Such materials can be bioabsorbable, if desired.

As noted above, spinal implant 100 also includes a plurality of staples 104. Returning to FIG. 1, in the depicted embodiment spinal implant 100 includes four staples 104a-104d. Each staple is of the same general design. In light of this, a general description of one of the staples will be given; it is appreciated that the staple design applies to all of the staples, except where noted otherwise.

Figure 6:
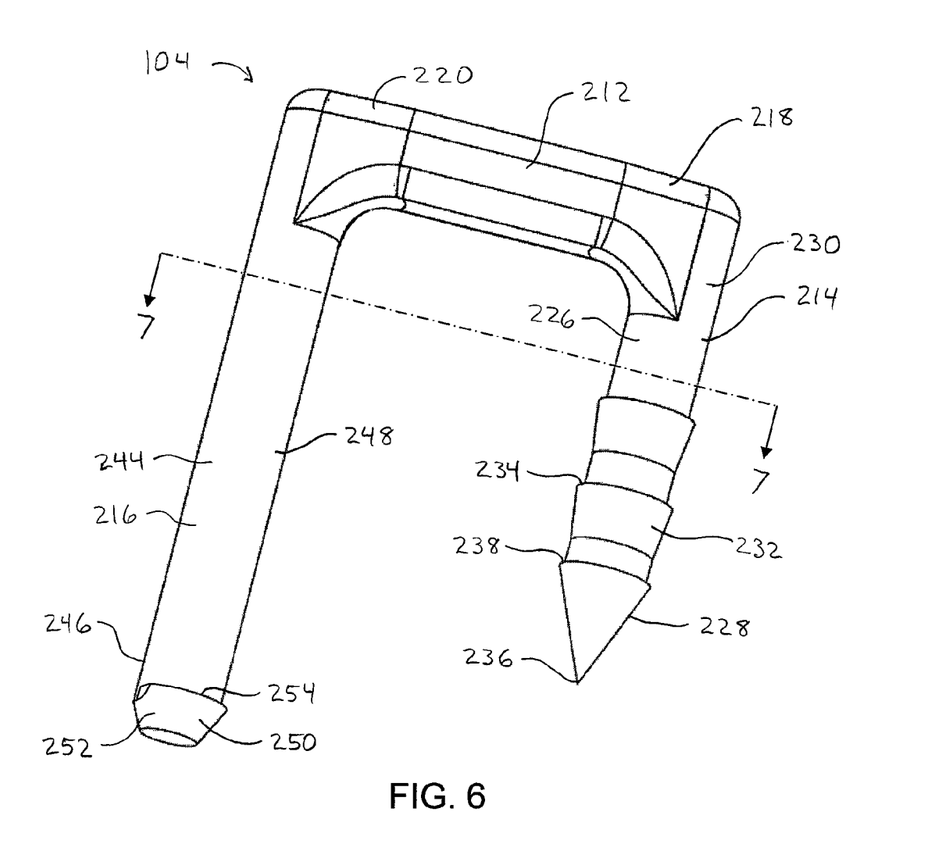
FIG. 6 is a perspective view of one of the staples shown in FIG. 1.
Figure 7:
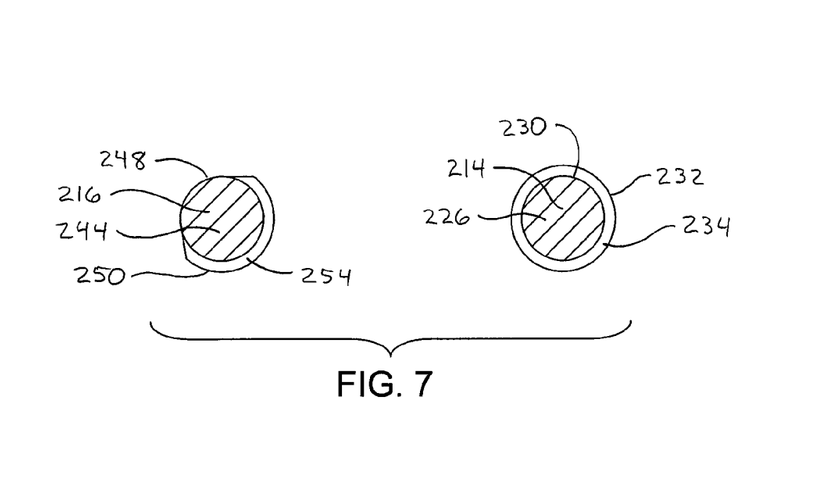
FIG. 7 is a cross sectional view of the staple shown in FIG. 6 taken along the sectional line 7-7.

Turning to FIGS. 6 and 7, staple 104 comprises a generally u-shaped body having three sections 212, 214, 216, each corresponding to a section of the "u" and lying in the same general plane. Each section has a generally circular cross-sectional shape, although this is not required. The first section 212, corresponding to the base of the "u", acts as a bridge between the other two sections and will therefore be identified herein as the bridge section. Bridge section 212 extends between a first end 218 and a spaced apart second end 220.

The second section 214 of staple 104, corresponding to one of the legs of the "u", is designed to be inserted into the bone and will therefore be identified herein as the bone insertion section. Bone insertion section 214 comprises a generally cylindrical first arm 226 that extends generally normally away from the first end 218 of bridge section 212 to a spaced apart distal end 228. The distal end 228 of first arm 226 can be conically shaped, ending at a point 236, to aid in inserting the staple 104 into the bone. First arm 226 has a generally smooth outer surface 230, although this is not required.

If desired, the outer surface 230 of the first arm 226 can have formed thereon or attached thereto surface features that will help the bone insertion section 214 remain within the bone, once inserted. For example, as shown in the depicted embodiment, annular barbs 232 are formed on the outer surface 230 of first arm 226 so as to encircle the first arm 226. Each barb 232 causes a lip 234 to be formed that faces proximally towards the bridge section 212. Lip 234 is designed to engage the bone after the first arm 226 has been inserted therein and prevent the first arm 226 from coming loose from the bone. As particularly shown in FIG. 7, barbs 232 fully encircle the first arm 226. Alternatively, barbs 232 can encircle any smaller portion thereof or can be comprised of separate radially spaced barb sections. Furthermore, first arm 226 can alternatively have a single barb or can incorporate multiple barbs, as in the depicted embodiment. As shown in the depicted embodiment, the distal end 228 of first arm 226 also includes a barb 238.

Returning to FIG. 6, the third section 216 of staple 104, corresponding to the other of the legs of the "u", is designed to be secured into spinal cage 102 and will therefore be identified herein as the cage insertion section. Cage insertion section 216 comprises a generally cylindrical second arm 244 that extends generally normally away from the second end 220 of bridge section 212 to a spaced apart distal end 246. Second arm 244 extends in generally the same direction as first arm 226 so as to be generally parallel thereto and to generally lie within the same plane. Similar to first arm 226, second arm 244 has a generally smooth outer surface 248, although this is not required. Second arm 244 has a cross sectional diameter that is equal to or slightly less than the width of the through hole 190 formed in the proximal end wall 110 of spinal cage 102 so as to be able to be slideably positioned therein.

Attached or otherwise formed at or near the distal end 246 of second arm 244 is a surface feature designed to prevent the cage insertion section from being completely detached from spinal cage 102 once inserted into through hole 190 of spinal cage 102. For example, a partially annular barb 250 is formed on the outer surface 248 of second arm 244 so as to partially encircle second arm 244 near distal end 246.

The barb 250 is shaped to have a slight slope 252 facing away from bridge section 212, which causes a lip 254 to be formed that faces proximally towards the bridge section 212. The outer diameter of the barb 250 is slightly greater than the diameter of the semicircular portions 200 and 202 of the through holes 190 formed in the proximal end wall 110 of spinal cage 102. As a result, once the second arm 244 has been inserted into through hole 190, the lip 254 will prevent second arm 244 from being completely withdrawn from spinal cage 102, as discussed below.

As particularly shown in FIG. 7, the barb 250 encircles about half of the circumference of second arm 244. Barb 250 is axially offset around second arm 244 so as to allow the outer surface 248 of second arm 244 to be able to bias against the outer surface 248 of a second arm 244 of an adjacent staple 104 having a mirror image of the barb 250 when both staples are disposed within through holes 190, as discussed in more detail below. As such, the barb 250 on cage insertion section 216 of any staple 104 can be as shown in FIG. 7 or can be positioned on second arm 244 as a mirror image of that shown on FIG. 7 (for example, contrast the positions of the barbs 250 on the two abutting staples 104 shown in FIG. 9). It is appreciated that instead of encircling about half of the circumference of the second arm 244, barb 250 can encircle a larger or smaller portion thereof. Furthermore, barb 250 can be comprised of separate radially spaced barb sections instead of a single uninterrupted section.

As noted above, cage insertion section 216 extends in generally the same direction from bridge section 212 as bone insertion section 214 so as to generally lie in the same plane. Hereinafter, this shall be referred to as the plane of the staple. As shown in FIG. 6, the cage insertion section 216 is generally longer than the bone insertion section 214, although this is not required.

Each staple 104 is typically made from a medical grade biocompatible metal, such as titanium, stainless steel, or the like. Other medical grade biocompatible metals having adequate strength, such as those discussed with spinal cage 102, can alternatively be used.

Figure 8:
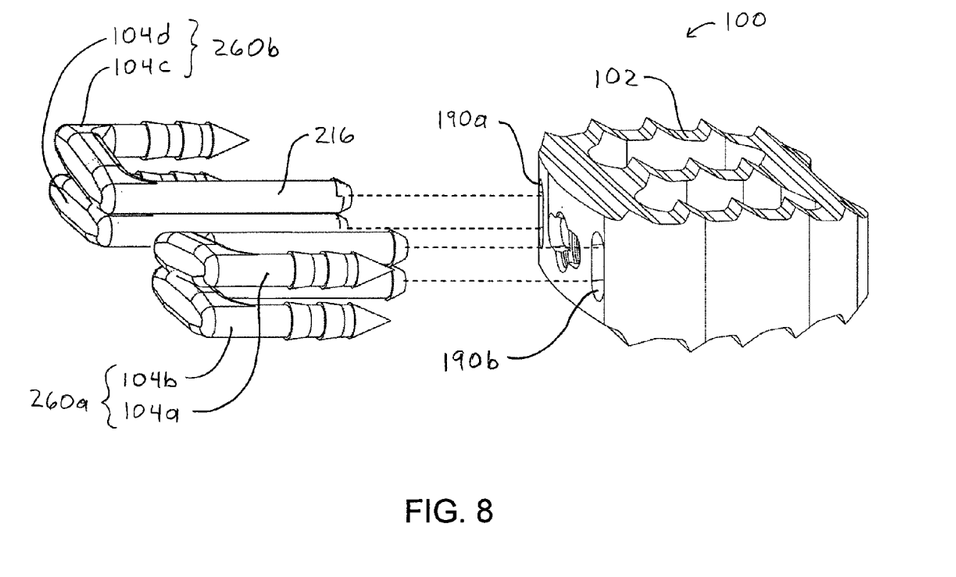
FIG. 8 is a perspective view of the spinal implant shown in FIG. 1 in a disassembled state, with the staples lying within the same general plane as the spinal cage.
Figure 9:
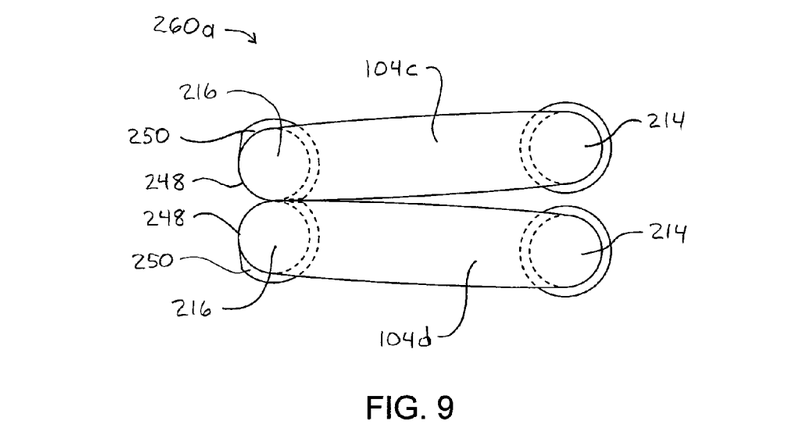
FIG. 9 is an end view of one of the staple pairs shown in FIG. 8 in a first position.

FIGS. 8-11 show one way to assemble spinal implant 100. As shown in FIG. 8, the four staples 104a-d are brought together as shown. Specifically, the staples 104 are positioned so as to form two pairs of staples 260a and 260b. The first pair 260a includes staples 104a and 104b, and the second pair 260b includes staples 104c and 104d. As shown in FIG. 9, in staple pair 260a, the barb 250 of the cage insertion sections 216 of the staples 104a and 104b are mirror images of each other, positioned on the staples so as to allow the outer surfaces of the cage insertion sections 216 of each staple 104a and 104b to be able to bias against each other along the length thereof. Returning to FIG. 8, the staples 104a and 104b are aligned in this first position so as to be lying on top of each other in generally parallel planes that are generally parallel to the top surface of spinal cage 102.

The second pair of staples 260b includes staples 104c and 104d which are also aligned in the first positions so as to be lying on top of each other in generally parallel planes, similar to first pair 260a. However, the second pair of staples 260b is positioned so as to face away from the first pair of staples 260a, as shown in the depicted embodiment.

The four staples 104a-d are positioned so that the cage insertion sections 216 thereof are aligned with the through holes 190 of the spinal cage 102. That is, cage insertion sections 216 of first pair of staples 260a are aligned with through hole 190b and cage insertion sections 216 of the second pair of staples 260b are aligned with through hole 190a.

Figure 10:
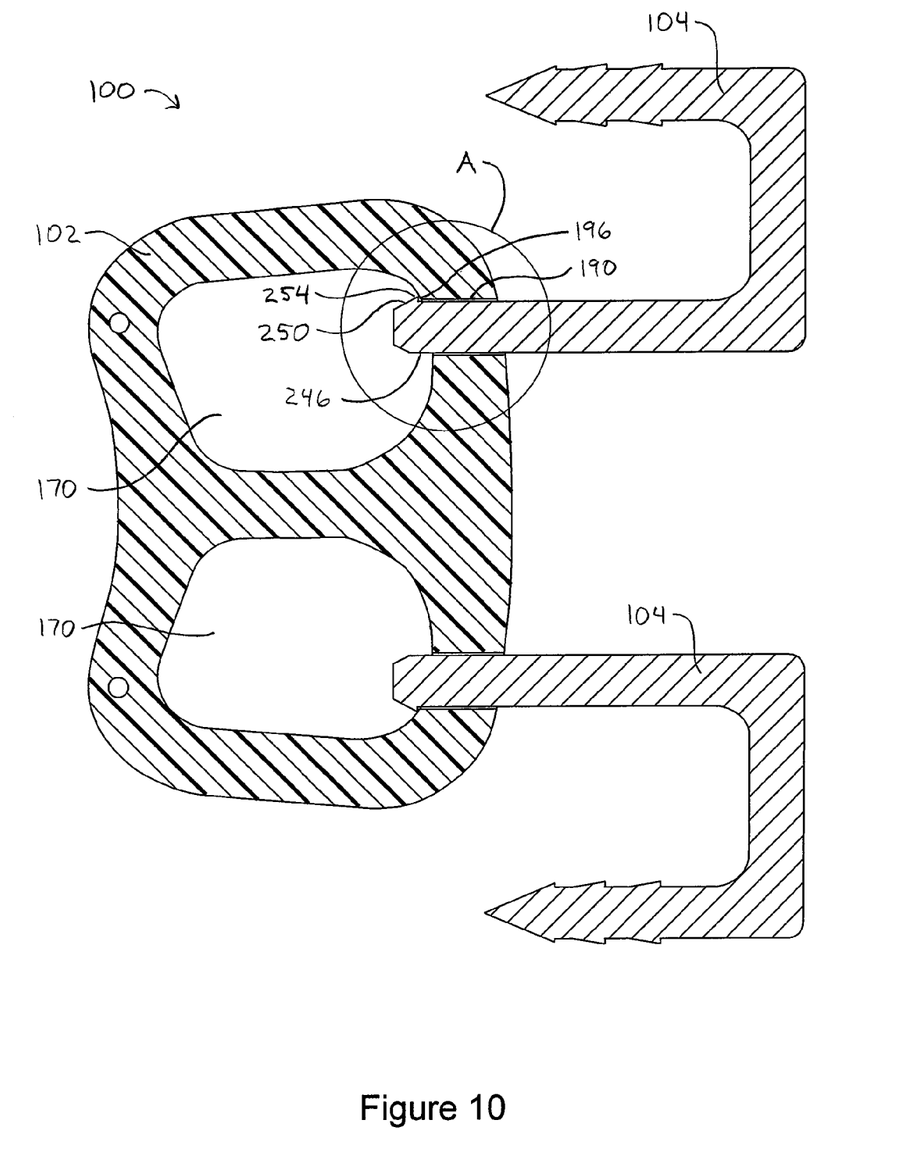
FIG. 10 is a cross sectional top view of the spinal implant shown in FIG. 8 with the staples inserted into the spinal cage.
Figure 11:
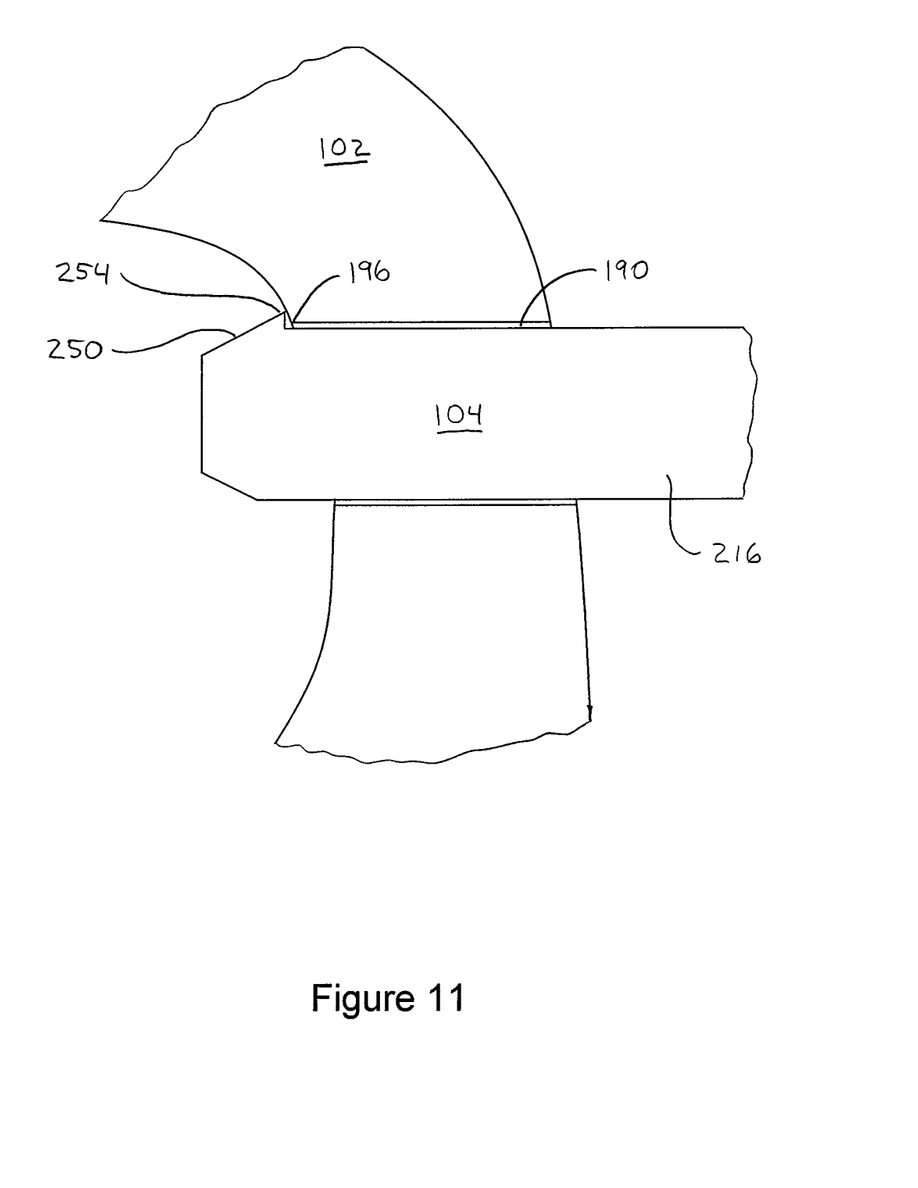
FIG. 11 is a close-up view of detail A of FIG. 10.

Turning to FIG. 10, to attach the staple pairs 260 to spinal cage 102, the distal end 246 of each cage insertion section 216 of each staple 104 is inserted into the corresponding through hole 190. The cage insertion section 216 is pushed into through hole 190 until barb 250 passes through through hole 190 and lip 254 has been moved into opening 170 past inside edge 196, as particularly shown in the close up view of FIG. 11. Because barb 250 has a slightly larger cross sectional diameter than through hole 190, lip 254 of barb 250 will thereafter catch on edge 196 when staple 104 is attempted to be withdrawn from through hole 190, thereby preventing staple 104 from detaching from spinal cage 102.

Figure 12:
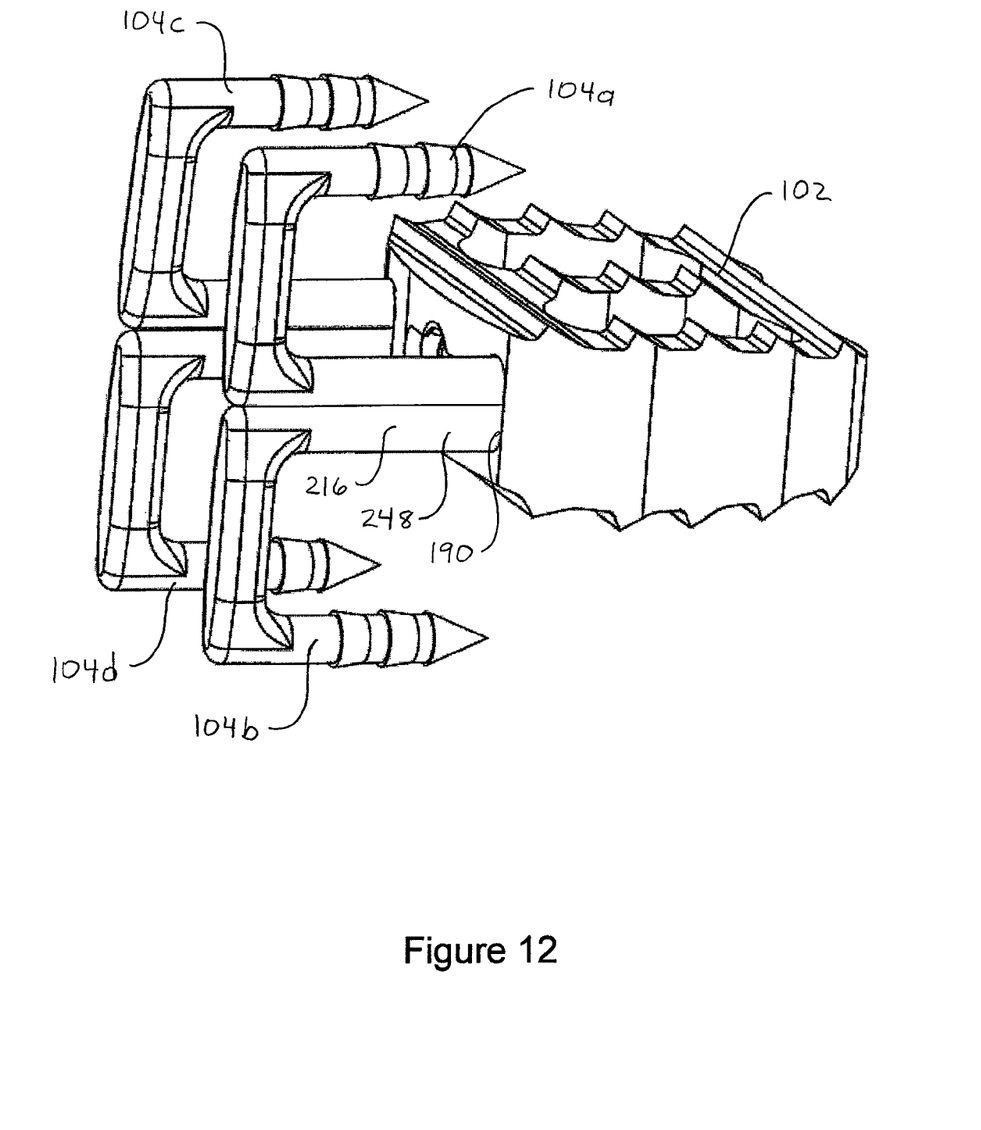
FIG. 12 is a perspective view of the spinal implant shown in FIG. 8, with the staples rotated to a second position so that each staple is generally orthogonal to the general plane of the spinal cage.
Figure 13:
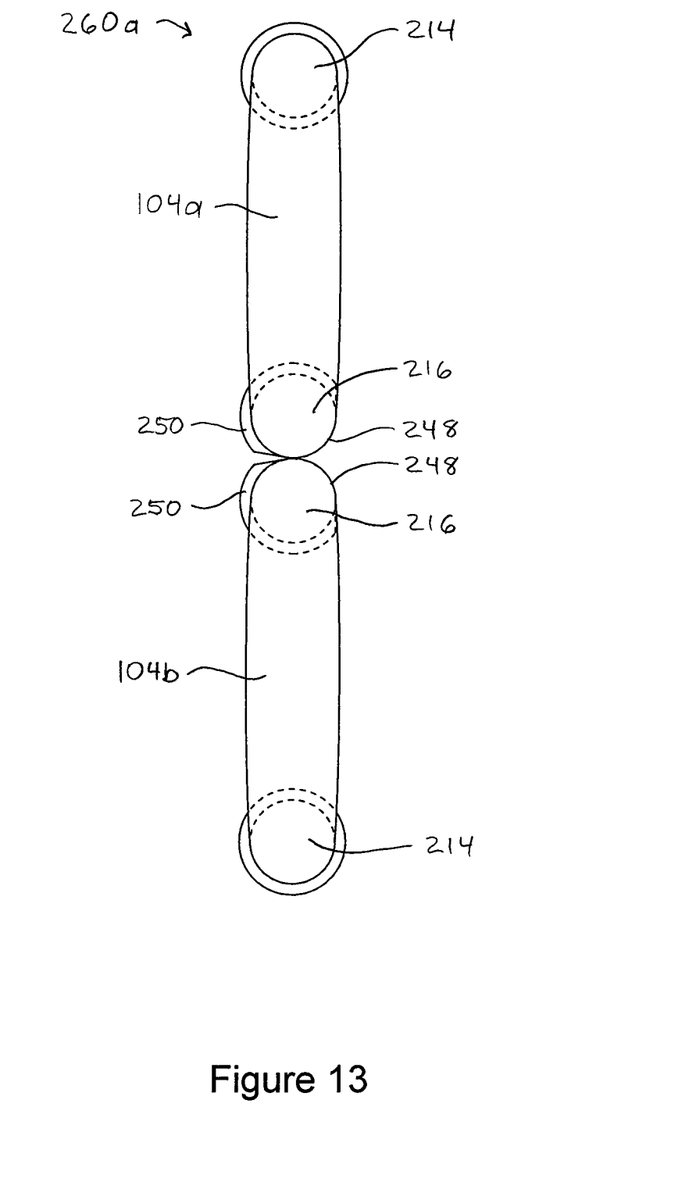
FIG. 13 is an end view of one of the staple pairs shown in FIG. 12.

FIGS. 12 and 13 show an alternative second positioning of the staples 104 within the staple pair 260 during assembly. Specifically, the staples 104 in one or both staple pairs 260 can be positioned in a second position so as to be aligned in the same plane relative to each other and generally orthogonal to the spinal cage 102 before being inserted into through hole 190. Because of the positioning of the barbs 250 on the cage insertion sections 216 of staples 104, the outer surfaces 248 of cage insertion sections 216 of staples 104a and 104b and 104c and 104d are again able to bias against each other along the length thereof in the second position.

It is appreciated that either staple 104 can be in other positions during assembly. For example, either staple can be rotated anywhere between the two positions discussed above and shown in FIGS. 9 and 13. Other positionings may also be possible, as long as the cage insertion sections 216 of each pair of staples 260a and 260b are respectively aligned with the through holes 190b and 190a before insertion. In addition, the four staples 104 can be positioned and inserted together, as shown in FIG. 8, or can be individually positioned and inserted.

Once assembled as described above, each staple 104 is freely rotatable about the cage insertion section 216 with respect to spinal cage 102 between the first positions, in which the plane of the staple 104 is substantially parallel to the plane of the top surface 180 of the spinal cage 102, and the second positions, in which the plane of the staple 104 is substantially orthogonal to the plane of the top surface 180 of the spinal cage 102. In the depicted embodiments, staples 104 are shown relative to the spinal cage in the first position in FIGS. 8 and 9 and in the second position in FIGS. 12 and 13.

Figure 14:
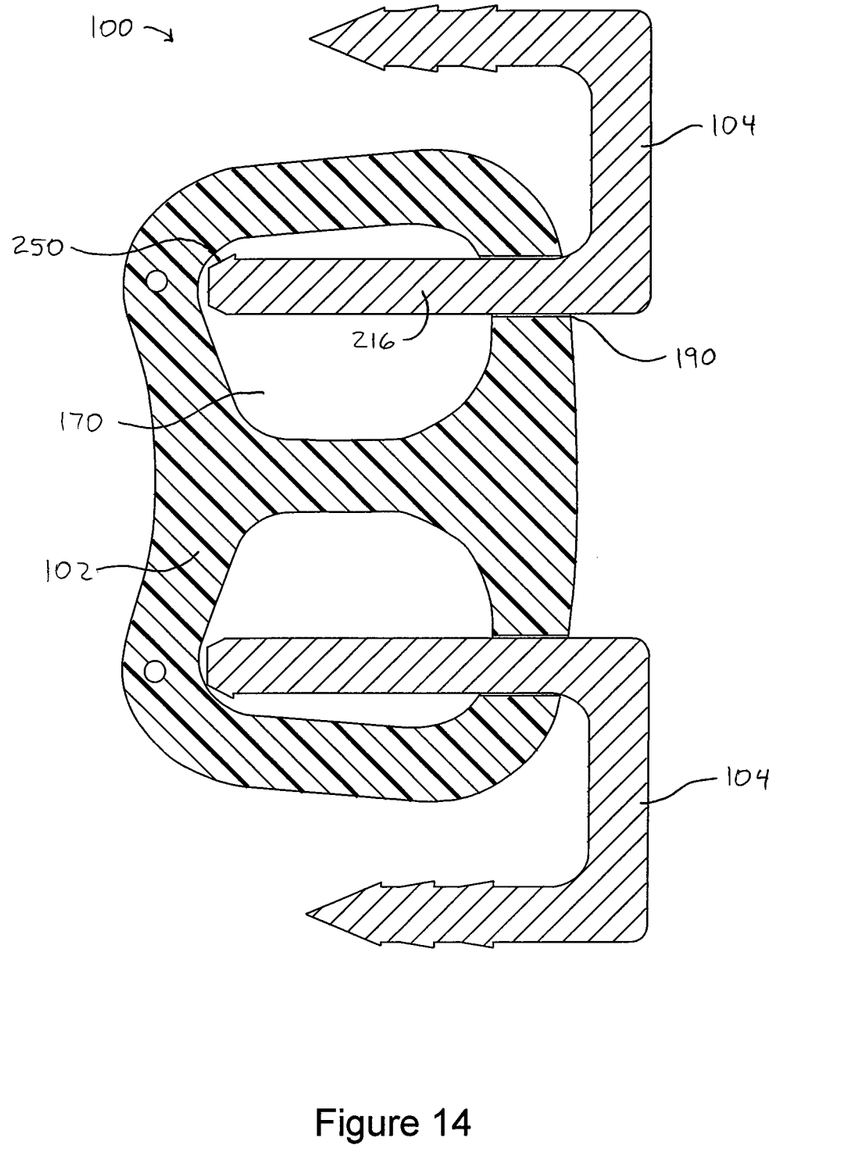
FIG. 14 is a cross sectional top view of the spinal implant shown in FIG. 8 with the staples fully inserted into the spinal cage.

Also once assembled, each staple 104 can be slid between a retracted position and a fully inserted position or occupy any position therebetween. In the retracted position, shown in FIG. 10, the lip 254 of barb 250 is adjacent to edge 196. In the fully inserted position, shown in FIG. 14, the cage insertion section 216 is inserted into the opening 170 as far as cage insertion section 216 will go. It is often desirable to position the staples 104 in the fully inserted position during the first stages of insertion of the spinal implant 100 into the body to provide a smaller footprint, thereby allowing easier manipulation of the implant 100 during positioning before actual insertion between vertebrae.

To insert assembled spinal implant 100 into the body, the intervertebral gap is prepared as is known in the art and the implant 100 is positioned adjacent to the intervertebral gap. As noted above, during movement of the spinal implant 100 to this position, it is often desirable to position the staples 104 in the fully inserted position, although this is not required. It is also often desirable to position each staple 104 in the first position, discussed above and shown in FIG. 10, so as to be generally parallel to the spinal cage 102, although this is also not required. Because of its stand-alone nature and compact size, the spinal implant 100 is especially suited to being used during anterior lumbar interbody fusion (ALIF) techniques in which the implant is inserted anteriorly into the intervertebral space. Alternatively, spinal implant 100 can be inserted using a transforminal lumbar interbody fusion (TLIF) technique or any other known intervertebral fusion technique.

Once the spinal implant 100 is in position adjacent to the intervertebral gap, the staples 104 are rotated, if needed, so as to be positioned in the second position, as shown in FIG. 12. In this position, each staple 104 is aligned with a portion of a vertebra (See, e.g., FIG. 15). Specifically, the insertion sections 214 of the upper two staples 104a and 104c are positioned so as to be insertable into the vertebra above the intervertebral gap and the lower two staples 104b and 104d are positioned so as to be insertable into the vertebra below the intervertebral gap.

Figure 15:
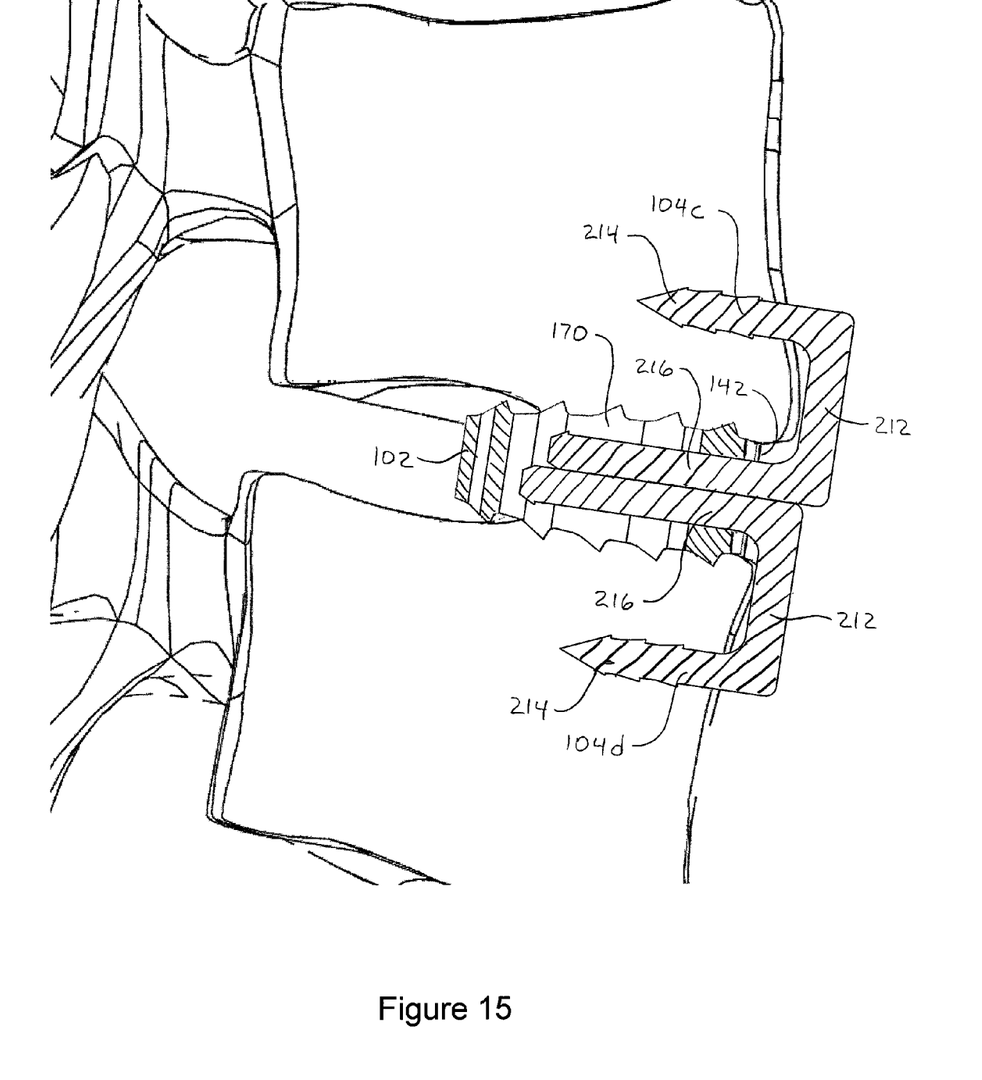
FIG. 15 is a cross sectional side view the spinal implant shown in FIG. 12, secured in a final position between vertebrae by the staples.

Once the spinal implant 100 is in position adjacent to the intervertebral gap, the staples 104 can also be retracted to the retracted position, as shown in FIG. 12. Once the staples 104 are in the retracted position, the spinal cage 102 can be inserted into the intervertebral gap, as shown in FIG. 15. The bone insertion sections 214 of the staples 104 are then securely inserted into the vertebrae above and below the intervertebral gap, where the barbs 238 help to prevent the detachment of the staple 104 from the bone. If desired, a hole can be pre-drilled into the bone and the bone insertion sections 214 can be inserted into the pre-drilled hole. Alternatively, the bone insertion section 214 can be hammered or otherwise forced into the bone without a pre-drilled hole.

As the bone insertion sections 214 are inserted into the vertebrae, the cage insertion sections 216 are caused to be inserted into openings 170 of spinal cage 102 by virtue of the shape of the staples 104. As such, when bone insertion sections 214 are fully inserted into the vertebrae, cage insertion sections 216 are also substantially fully inserted into openings 170, as shown in FIG. 15. As a result, bridge sections 212 can contact exterior side surface 142 of proximal end wall 110. This prevents spinal cage 102 from exiting the intervertebral gap or moving laterally therein.

If desired, the openings 170 of spinal cage 102 can be packed with an osteogenic substance prior to insertion within the body to promote the rapid growth of a bony column between the adjacent vertebrae. Because of the typically spongy consistency of the osteogenic material, insertion of the cage insertion sections 216 into the openings 170 is still easily accomplished.

The present invention may be embodied in other specific forms without departing from its spirit or essential characteristics. Accordingly, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A spinal implant comprising:
   a spinal cage configured to be positioned in an intervertebral space between adjacent vertebrae, the spinal cage comprising a top surface and an opposing bottom surface that extend between a proximal end face and an opposing distal end face and that extend between opposing side faces, a first and second through hole each extending into the proximal end face;
   a first pair of staples, each staple of the first pair having a substantially U-shaped configuration and comprising a bone insertion section, a cage insertion section and a bridge extending therebetween, the cage insertion section of each of the first pair of staples being rotatably disposed within the first through hole of the spinal cage so that each bone insertion section thereof can rotate outside of the spinal cage between alignment with one of the side faces of the spinal cage and alignment with one of the top surface or bottom surface of the spinal cage; and
   a second pair of staples, each staple of the second pair having a substantially U-shaped configuration and comprising a bone insertion section, a cage insertion section and a bridge extending therebetween, the cage insertion section of each of the second pair of staples being rotatably disposed within the second through hole of the spinal cage so that each bone insertion section thereof can rotate outside of the spinal cage between alignment with one of the side faces of the spinal cage and alignment with one of the top surface or bottom surface of the spinal cage.

2. The spinal implant recited in claim 1, wherein the spinal cage comprises:
   a proximal end wall;
   a spaced apart distal end wall; and
   a plurality of spaced apart beams extending between the proximal and distal end walls so as to bound one or more openings extending completely through the spinal cage.

3. The spinal implant recited in claim 2, wherein the first and second through holes are formed on the proximal end wall of the spinal cage so as to communicate with the one or more openings.

4. The spinal implant recited in claim 3, wherein the first pair staples are slidably disposed within the first through hole.

5. The spinal implant recited in claim 1, wherein the spinal cage comprises a means for receiving an inserter device.

6. The spinal implant recited in claim 1, further comprising one or more barbs formed on the bone insertion section of at least one of the first pair of staples.

7. The spinal implant recited in claim 1, wherein a barb is formed on the cage insertion sections of the first pair of staples to prevent the staples from being completely withdrawn from the first through hole while allowing the first pair of staples to be slidable within the first through hole.

8. The spinal implant recited in claim 1,
   wherein the first pair of staples are secured within the first through hole of the spinal cage so as to be nonremovable therefrom, and
   wherein, while secured within the first through hole, each staple is longitudinally slidable within the first through hole relative to the spinal cage between.

9. The spinal implant recited in claim 1, wherein the cage insertion section of the first pair of staples has a length extending from the bridge to a terminal tip and the bone insertion section of the first pair of staples has a length extending from the bridge to a terminal tip, the length of the cage insertion section being longer than the length of the bone insertion section for each of the first pair of staples.

10. A spinal implant comprising:
    a spinal cage configured to be positioned in an intervertebral space between adjacent vertebrae, the spinal cage comprising a top surface and an opposing bottom surface that extend between a proximal end face and an opposing distal end face and that extend between opposing side faces, a first through hole being formed on the proximal end face so as to extend into the spinal cage; and
    a first pair of staples, each staple of the first pair having a substantially U-shaped configuration and comprising a bone insertion section, a cage insertion section and a bridge extending therebetween, the cage insertion section of each of the first pair of staples being rotatably disposed within the first through hole of the spinal cage so that each bone insertion section thereof can rotate outside of the spinal cage between alignment with one of the side faces of the spinal cage and alignment with one of the top surface or bottom surface of the spinal cage, each staple of the first pair also having a lip radially outwardly projecting from each cage insertion section, the lips biasing against each other when the bone insertion sections are in the alignment with one of the top surface or bottom surface of the spinal cage so as to preclude further rotation of the bone insertion sections away from the one of the side faces.

11. The spinal implant recited in claim 10, wherein for each staple of the first pair, the bone insertion section is longer than the cage insertion section.

12. The spinal implant recited in claim 10, wherein the lip of each staple of the first pair comprises a portion of a tapered barb disposed on each cage insertion section.

13. The spinal implant recited in claim 10, wherein an opening is formed in the top or bottom surface of the spinal cage, the opening being configured to receive an osteogenic material.

14. The spinal implant recited in claim 13, wherein the opening extends completely through the spinal cage between the top and bottom surfaces.

15. The spinal implant recited in claim 10, wherein a second through hole is formed on the proximal end face so as to extend into the spinal cage, and wherein the spinal implant further comprises a second pair of staples each having a bridge section and a pair of legs extending from opposing ends of the bridge section so as to be substantially U-shaped, one of the legs of each of the second pair of staples being slidably inserted into the second through hole.

16. The spinal implant recited in claim 10, wherein the cage insertion section of each first pair of staples is slidably disposed within the first through hole.

17. The spinal implant recited in claim 10, further comprising a plurality of barbs formed on at least one of the top and bottom surfaces of the spinal cage.

* * * * *